(12) United States Patent
Sharif et al.

(10) Patent No.: US 6,649,655 B2
(45) Date of Patent: Nov. 18, 2003

(54) 11β-FLUORO 15β-HYDROXY PGF$_{2α}$ ANALOGS AS FP RECEPTOR ANTAGONISTS

(75) Inventors: Najam A. Sharif, Arlington, TX (US); Brenda W. Griffin, Colleyville, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 10/202,230

(22) Filed: Jul. 24, 2002

(65) Prior Publication Data

US 2003/0083375 A1 May 1, 2003

Related U.S. Application Data

(63) Continuation of application No. 09/210,976, filed on Dec. 14, 1998, now Pat. No. 6,441,033.
(60) Provisional application No. 60/068,468, filed on Dec. 22, 1997.

(51) Int. Cl.[7] ............................................. A61K 31/215
(52) U.S. Cl. ........................................ 514/530; 514/573
(58) Field of Search .................................. 514/530, 573

(56) References Cited

U.S. PATENT DOCUMENTS

| 4,321,275 A | 3/1982 | Bowler |
| 4,870,104 A | 9/1989 | Vorbruggen et al. |

FOREIGN PATENT DOCUMENTS

| EP | 364417 B1 | 4/1990 |

OTHER PUBLICATIONS

Berridge, *Inositol trisphosphate and calcium signalling* Nature 361:315–325 (Jan. 1993).

Coleman et al., *Prostanoids and their receptors*, in *Comprehensive Medicinal Chemistry: The Rational Design, Mechanistic Study and Therapeutic Application of Chemical Compounds* (Hansch, C., Sammes, P.G., Taylor, J.B., Eds.) (Pergamon Press: New York, (Oxford)) 3:674 (1990).

Coleman et al., *VIII International Union of Pharmacology classification of prostanoid receptors: Properties, distribution, and structure of the receptors and their subtypes,* Pharmacol. Rev., 46:205–229 (1994).

Davis et al., *Prostaglandin F$_{2α}$ stimulates phosphatidylinositol 4,5–bisphosphate hydrolysis and mobilizes intracellular Ca$^{2+}$ in bovine luteal cells,* Proc. Natl. Acad. Sci., (USA) 84:3728–3732 (Jun. 1987).

Delaey and Van de Voorde, *Prostanoid–induced contractions are blocked by sulfonylureas*, Eur. J. Pharmacol., 280:179–184 (1995).

Fitzpatrick et al., *Antagonism of the pulmonary vasoconstrictor response to prostaglandin F$_{2α}$ by N–dimethylamino substitution of prostaglandin F$_{2α}$*, J. Pharmacol. Exp. Ther., 206(1):139–142 (1978).

Griffin et al., *FP prostaglandin receptors mediating inositol phosphates generation and calcium mobilization in Swiss 3T3 Cells: A pharmacological study,* J. Pharmacol. Exp. Ther., 281(2):845–854 (1997).

Kitanaka et al., *Phloretin as an antagonist of prostaglandin F$_{2α}$ receptor in cultured rat astrocytes,* J. Neurochem., 60(2):704–708 (1993).

Maddox et al., *Amide and I–amino derivatives of F prostaglandins as prostaglandin antagonists,* Nature, 273: 549–552 (Jun. 1978).

Nakao et al., *Characterization of prostaglandin F$_{2α}$ receptor of mouse 3T3 fibroblasts and its funtional expression in Xenopus laevis oocytes,* J. Cell. Physiol., 155: 257–264 (1993).

*Primary Examiner*—Zohreh Fay
(74) *Attorney, Agent, or Firm*—Barry L. Copeland

(57) ABSTRACT

Methods and compositions for the antagonism of FP receptor-mediated biological responses are disclosed.

16 Claims, 5 Drawing Sheets

Schild Analysis for Compound III as an FP Receptor Antagonist

Inhibition of Human Ocular FP Receptor Functional Response by Increasing Concentrations of Compound III

11β-FLUORO 15β-HYDROXY PGF$_{2\alpha}$ ANALOGS AS FP RECEPTOR ANTAGONISTS

RELATED APPLICATIONS

The present application is a continuation application of U.S. patent application Ser. No. 09/210,976, filed on Dec. 14, 1998, now U.S. Pat. No. 6,441,033, which claims the benefit of Provisional application Ser. No. 60/068,468, filed Dec. 22, 1997.

FIELD OF THE INVENTION

The FP prostaglandin receptor belongs to a family of prostaglandin receptors, all of which have seven-transmembrane domains and couple to specific G-proteins. When activated by the binding of a specific ligand (a prostaglandin belonging to one of several defined classes of prostaglandins) the G-proteins transmit and amplify within the cell a signal to their preferred prostaglandin receptors on the surface of the cell membrane. (Coleman et al., *VIII International Union of Pharmacology classification of prostanoid receptors; Properties, distribution, and structure of the receptors and their subtypes, Pharmacol. Rev.,*] 46:205–229 (94)). Ligand-induced activation of the FP prostaglandin receptor is believed to involve activation of the enzyme phospholipase C (mediated by specific G-proteins), resulting in rapid hydrolysis of phosphatidylinositol 4,5-bisphosphate in the cell membrane. The products of this hydrolysis are inositol 1,4,5-trisphosphate (IP$_3$) and diacylglycerol (DAG), which act as second messengers inside the cell. (Coleman et al., *VIII International Union of Pharmacology classification of prostanoid receptors: Properties, distribution, and structure of the receptors and their subtypes, Pharmacol. Rev.,* 46:205–229 (1994); Berridge, *Inositol trisphosphate and calcium signalling Nature* 361:315–325 (1993); Davis et al., *Prostaglandin F$_{2\alpha}$ stimulates phosphatidylinositol 4,5-bisphosphate hydrolysis and mobilizes intracellular Ca$^{2+}$ in bovine luteal cells, Proc. Natl. Acad. Sci.,* (USA) 84:3728–3732 (1987); Nakao et al., *Characterization of prostaglandin F$_{2\alpha}$ receptor of mouse 3T3fibroblasts and its functional expression in Xenopus laevis oocytes, J. Cell. Physiol.,* 155:257–264 (1993); and Griffin et al., *FP prostaglandin receptors mediating inositol phosphates generation and calcium mobilization in Swiss 3T3 Cells: A pharmacological study, J. Pharmacol. Exp. Ther.,* 281: 845–854 (1997)). IP$_3$ mobilizes Ca++ from intracellular stores and DAG activates protein kinase C. Together these second messengers activate various enzymes and other proteins to produce the final biological responses. The latter may involve tissue contraction, hormone release, fluid secretion, or initiation of an inflammatory response.

Like most prostaglandin receptors, the FP prostaglandin receptor is broadly distributed in human and animal tissues. Various endogenous prostaglandins, arising from the action of cyclooxygenases on arachidonic acid, can bind to and activate the FP receptor, with prostaglandin F$_{2\alpha}$ (PGF$_{2\alpha}$) being the most potent FP agonist of these endogenous ligands. Therapeutic applications of FP receptor activation using such endogenous prostaglandins are known. (Coleman et al., *Prostanoids and their receptors,* in *Comprehensive Medicinal Chemistry: The Rational Design, Mechanistic Study and Therapeutic Application of Chemical Compounds* (Hansch, C., Sammes, P. G., Taylor, J. B., Eds.) (Pergamon Press: New York, (Oxford)) 3:674 (1990); and Coleman et al., *VIII International Union of Pharmacology classification of prostanoid receptors: Properties, distribution, and struc-ture of the receptors and their subtypes, Pharmacol. Rev.,* 46:205–229 (1994)).

Characterization of the functions of the various prostaglandin receptors has been advanced by the availability of synthetic analogs of the endogenous prostaglandins. Many such analogs have been prepared and described in the literature. (Coleman et al., *Prostanoids and their receptors,* in *Comprehensive Medicinal Chemistry: The Rational Design, Mechanistic Study and Therapeutic Application of Chemical Compounds* (Hansch, C., Sammes, P. G., Taylor, J. B., Eds.) (Pergamon Press: New York, (Oxford)) 3:674 (1990).

In general, rational design of structural analogs of the endogenous prostaglandins based on empirically-derived structure-activity relationships has resulted in more potent and more selective agonists at the various prostaglandin receptors. The availability of well-characterized potent and selective agonists at the FP and other prostaglandin receptors has increased understanding of the in vivo pharmacological (and potential therapeutic) actions of both the specific prostaglandin analogs and the specific prostaglandin receptors to which they bind. However, it has now been discovered that potent and selective prostaglandin receptor antagonists serve a complementary function in defining the physiologic and pharmacological roles of prostaglandin receptors, and in certain instances are themselves valuable therapeutic agents.

There are only a few classes of prostaglandin receptors for which antagonists with defined chemical structures and well-characterized antagonistic biological activities have been identified. (Coleman et al., *VIII International Union of Pharmacology classification of prostanoid receptors: Properties, distribution, and structure of the receptors and their subtypes, Pharmacol. Rev.,* 46:205–229 (1994)). For the FP receptor, compounds suggested to be or classified as antagonists include the dimethylamide and dimethylamine of PGF$_{2\alpha}$ (Maddox et al., *Amide and i-i amino derivatives of F prostaglandins as prostaglandin antagonists, Nature,* 273:549–552 (1978); (Fitzpatrick et al., *Antagonism of the pulmonary vasoconstrictor response to prostaglandin F$_{2\alpha}$ by N-dimethylamino substitution of prostaglandin F$_{2\alpha}$ J. Pharmacol. Exp. Ther.,* 206:139–142 (1978)) phloretin (Kitanaka et al., *Phloretin as an antagonist of prostaglandin F$_{2\alpha}$ receptor in cultured rat astrocytes, J. Neurochem.,* 60:704–708 (1993)), glybenclamide and tolbutamide (Delaey and Van de Voorde, *Prostanoid-induced contractions are blocked by sulfonylureas, Eur. J. Pharmacol.,* 280:179–184 (1995)). Most of these compounds, however, are either inactive or very weak FP prostaglandin receptor antagonists with little or no selectivity at the FP prostaglandin receptor.

There remains a need, therefore, for potent and selective antagonists of the FP prostaglandin receptor that can be used for the general purposes of: 1) defining more precisely the function(s) of the FP prostaglandin receptor and its selective agonists in vivo and in vitro (e.g., as valuable pharmacological tools); 2) serving as a diagnostic tool for FP prostaglandin receptor function in various disease processes; 3) treating various conditions, diseases or untoward effects associated with FP receptor activation, such as ocular hyperemia, cystoid macular edema, iris hyperpigmentation or melanogenesis, excessive bone deposition, and premature labor.

SUMMARY OF THE INVENTION

The present invention is directed to the use of certain 11β-fluoro-15β-hydroxy PGF$_{2\alpha}$ analogs to antagonize FP receptor-mediated biological responses.

DETAILED DESCRIPTION OF THE INVENTION

Figure 1:
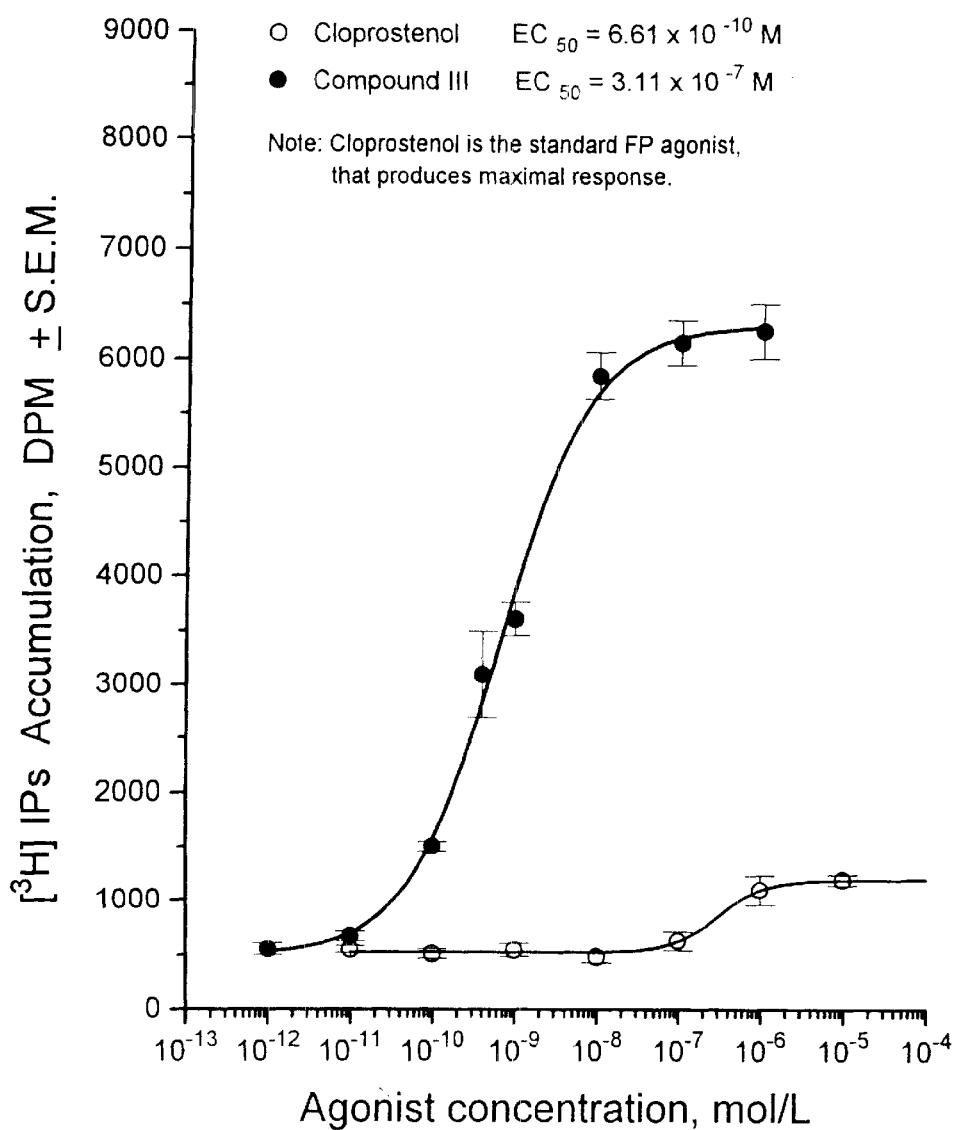
FIG. 1 is a graphical depiction of the concentration-dependent stimulation of the FP receptor by a standard FP agonist, cloprostenol, and Compound III on A7r5 cells and the consequential production of [$^3$H]IPs quantified by ion exchange chromatography.

It has unexpectedly been found that the 11β-fluoro-15β-hydroxy PGF$_{2α}$ analogs of the present invention act as potent FP receptor antagonists, having utility as pharmacologic and diagnostic tools as well as true therapeutics. Specifically, the FP receptor antagonists of the present invention may be used for the general purposes of: 1) defining more precisely the function(s) of the FP prostaglandin receptor and its selective agonists in vivo and in vitro (e.g., as valuable pharmacological tools); 2) serving as a diagnostic tool for FP prostaglandin receptor function in various disease processes; 3) treating various to conditions, diseases or untoward effects associated with FP receptor activation, such as ocular hyperemia, cystoid macular edema, iris hyperpigmentation or melanogenesis, excessive bone deposition, and premature labor.

The substituted PGF$_{2α}$ analogs useful in the methods and compositions of the present invention have the following formula I:

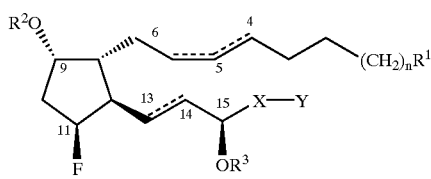

wherein:

$R^1$=CO$_2$R, CONR$^4$R$^5$, CH$_2$OR$^6$, or CH$_2$NR$^7$R$^8$; where:
R=H or cationic salt moiety, or CO$_2$R= pharmaceutically acceptable ester moiety; R$^4$, R$^5$=same or different=H or alkyl; R$^6$=H, acyl, or alkyl; R$^7$, R$^8$=same or different=H, acyl, or alkyl; with the proviso that if one of R$^7$, R$^8$=acyl, then the other=H or alkyl;

n=0 or 2;

$R^2$, $R^3$=same or different H, alkyl, or acyl;

----=single or non-cumulated double bond, with the provisos that if a double bond is present between carbons 4 and 5, it is of the cis configuration; and that if a double bond is present between carbons 13 and 14, it is of the trans configuration;

X=(CH$_2$)$_m$ or (CH$_2$)$_m$O, where m=1–6; and

Y=phenyl, optionally substituted with alkyl, halo, trihalomethyl, alkoxy, acyl, acyloxy, amino, alkylamino, acylamino, or hydroxy; or X-Y=(CH$_2$)$_p$Y$^1$; where p=0–6; and

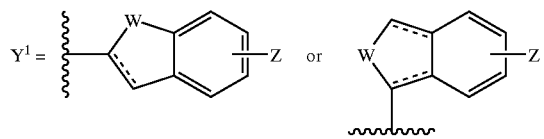

wherein:

W=CH$_2$, O, S(O)$_q$, NR$^{10}$, CH$_2$CH$_2$, CH=CH, CH$_2$O, CH$_2$S(O)$_q$, CH=N, or CH$_2$NR$^9$;

where q=0–2, and R$^{10}$=H, alkyl, or acyl;

Z=H, alkyl, alkoxy, acyl, acyloxy, halo, trihalomethyl, amino, alkylamino, acylamino, or hydroxy; and ----=single or double bond.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "alkoxy" represents an alkyl group attached through an oxygen linkage.

The term "alkylamino" represents an alkyl group attached through a nitrogen linkage.

The term "dialkylamino" represents two alkyl groups attached through a nitrogen linkage.

The term "lower alkyl" represents alkyl groups containing one to six carbons (C1–C6).

The term "halogen" represents fluoro, chloro, bromo, or iodo.

The term "aryl" refers to carbon-based rings which are aromatic. Aromatic rings have alternating double and single bonds between an even number of atoms forming a system which is said to 'resonate'. The rings may be isolated, such as phenyl, or fused, such as naphthyl. The ring hydrogens may be substituted with other groups, such as lower alkyl, or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

For purposes of the foregoing and following definitions, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Preferred are alkyl esters. Most preferred are $C_2$–$C_4$ alkyl esters, and especially isopropyl esters. In addition, references to specifically numbered carbons, e.g. "carbons 4 and 5" or "carbons 5 and 6", shall mean the carbons so designated in the structural formulas even when n=2.

Preferred for use in the methods and compositions of the present invention are those compounds of formula I above, wherein:

$R^1$=$CO_2R$, where R=H; or $CO_2R$ pharmaceutically acceptable ester moiety;

n=0;

$R^2$=$R^3$=H;

----=single or non-cumulated double bond, with the provisos that if double bond is present between carbons 4 and 5 or carbons 5 and 6, it is of the cis configuration; and that if a double bond is present between carbons 13 and 14, it is of the trans configuration;

X=$CH_2O$ or $CH_2CH_2$;

Y=phenyl, optionally substituted with halo or trihalomethyl; or

X-Y=$(CH_2)_pY^1$; where p=0; and $Y^1 =$ 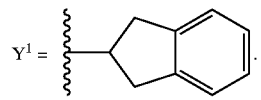

Especially preferred for use in the present invention are the following compounds:

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Ed., Academic Press Publishers: New York, 1983–1985 (five volumes published over a three year span with chapters contributed by about two dozen authors) and *Principles of Asymmetric Synthesis* by R. E. Gawley and J. Aube, Ed., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC,* G. Subramanian, Ed., VCH Publishers: New York, 1994; *Chiral Separations by HPLC,* A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions* volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios. Also included within the scope of the invention are the individual isomers substantially free of their enantiomers.

In the foregoing illustrations, as well as those provided hereinafter, wavy line attachments indicate either the alpha (α) or beta (β) configuration. The carbon numbering is as indicated in structural formula I, even when n=2. A hatched line, as used e.g. at carbon 9, indicates the α configuration. A solid triangular line indicates the β configuration. Dashed lines on bonds, e.g. between carbons 5 and 6, indicate a single or double bond. Two solid lines between carbons indicate a double bond of the specified configuration.

| Compound Number | Compound Name | Compound Structure |
|---|---|---|
| II | (5Z,13E)-(9S,11S,15R)-9,15-Dihydroxy-11-fluoro-15-(2-indanyl)-16,17,18,19,20-pentanor-5,13-prostadienoic acid isopropyl ester | 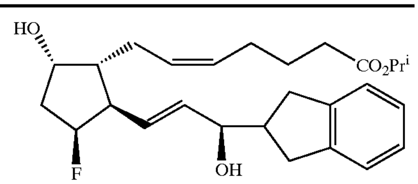 |
| III | (5Z,13E)-(9S,11S,15R)-9,15-Dihydroxy-11-fluoro-15-(2-indanyl)-16,17,18,19,20-pentanor-5,13-prostadienoic acid | 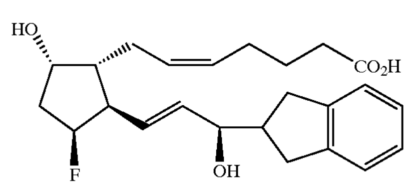 |

Other related $PGF_{2\alpha}$ analogs within the scope of the present invention are known and their syntheses are either described in the literature or can be achieved by methods similar to those described in the literature or otherwise known to those of skill in the art. See, for example, U.S. Pat. Nos. 4,321,275 and 4,870,104, and EP 364417 B1. The foregoing references are by this reference incorporated herein.

In the following Examples 1–2, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of II

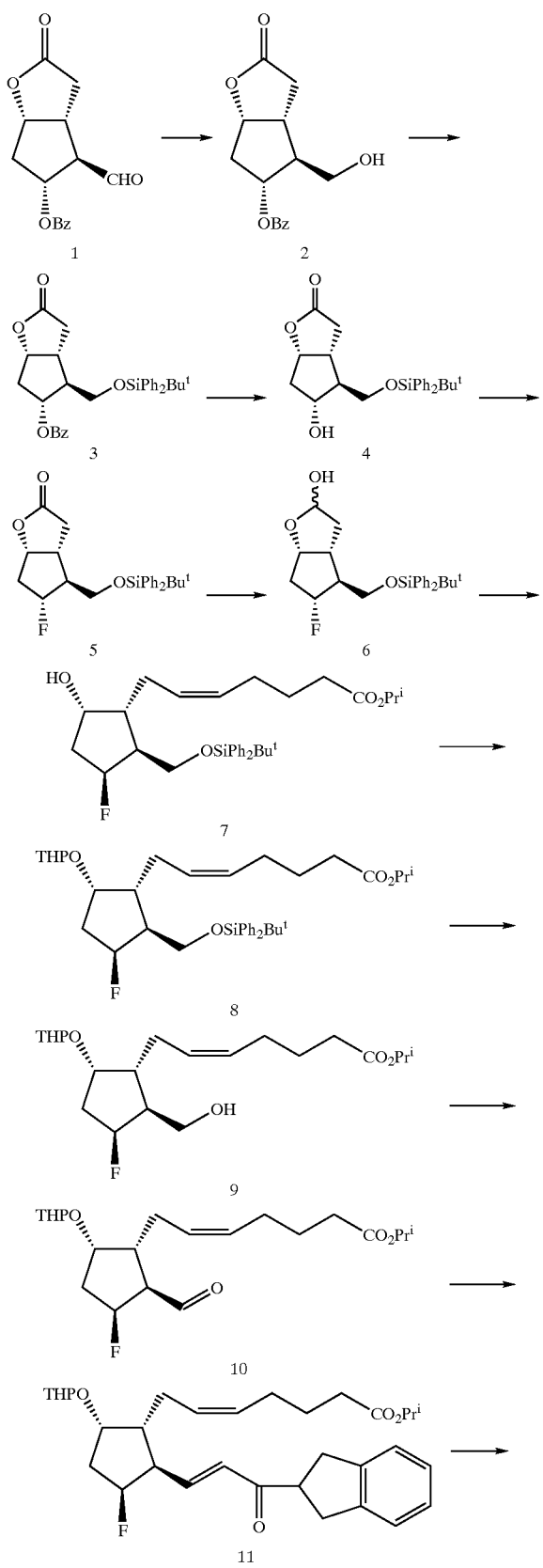

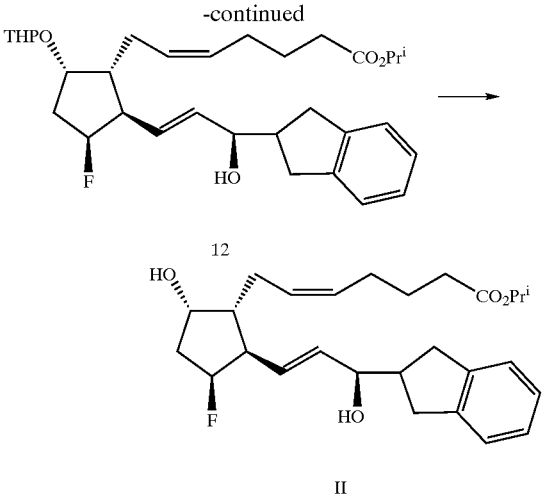

A. (3aR,4R,5R,6aS)-5-Benzoyloxy-4-(hydroxymethyl)hexahydro-2H-cyclopenta[b]furan-2-one (2)

To a suspension of sodium borohydride (650 mg, 17.1 mmol) in methanol (20 mL) at 0° C. (bath temperature) was added a solution of (3aR,4R,5R,6aS)-5-(benzoyloxy)hexahydro-2H-cyclopenta[b]furan-2-one-4-carboxaldehyde (1) (3.5 g, 12.8 mmol) as a solution in 1:1 methanol:methylene chloride (40 mL). After 25 min, saturated citric acid was added cautiously (60 mL), the mixture was extracted with ethyl acetate (3×40 mL), the combined organic layers were washed with water (2×80 mL) and saturated brine (2×80 mL), dried (magnesium sulfate), filtered, and concentrated to afford 2 (2.43 g, 69%).

B. (3aR,4R,5R,6aS)-5-Benzoyloxy-4-[(t-butyldiphenylsiloxy)methyl]hexahydro-2H-cyclopenta[b]furan-2-one (3)

To a solution of 2 (2.40 g, 8.8 mmol), 4-(dimethylamino)pyridine (100 mg, 0.82 mmol), and imidazole (1.00 g, 14.7 mmol) in methylene chloride (35 mL) was added dropwise t-butyldiphenylchlorosilane (2.85 g, 10.4 mmol). After stirring overnight, the mixture was added to saturated ammonium chloride (40 mL), extracted with ethyl acetate (3×40 mL), dried (magnesium sulfate), filtered, concentrated, and chromatographed on a 14 cm tall×53 mm diameter silica gel eluting with 30% ethyl acetate in hexane to afford 3 (3.776 g, 83%).

C. (3aR,4R,5R,6aS)-4-[(t-Butyldiphenylsiloxy)methyl]-5-hydroxyhexahydro-2H-cyclopenta[b]furan-2-one (4)

To a solution of 3 (15.7 g, 30.0 mmol) in methanol (100 mL) was added potassium carbonate (4.14 g, 30.0 mmol). After 1 h, saturated ammonium chloride (100 mL) and saturated brine (100 mL) were added, the mixture was extracted with methylene chloride (3×100 mL), dried (magnesium sulfate), filtered, concentrated, and chromatographed on a 15 cm tall×41 mm diameter silica gel column eluting with 40% ethyl acetate in hexane to afford 4 (9.93 g, 79%).

D. (3aR,4R,5S,6aS)-4-[(t-Butyldiphenylsiloxy)methyl]-5-fluorohexahydro-2H-cyclopenta[b]furan-2-one (5)

To a solution of (diethylamino)sulfur trifluoride (4.62 g, 28.6 mmol) in methylene chloride (27 mL) at −60° C. was added a solution of 4 (10.7 g, 26 mmol) dropwise as a solution in methylene chloride (27 mL). After 30 min, the reaction was warmed to room temperature and was stirred for an additional 18 h. To the solution was then cautiously added saturated sodium bicarbonate, the phases were separated, the aqueous layer was extracted with methylene chloride, the combined organic layers were dried (sodium sulfate), filtered, concentrated, and chromatographed on 300 g of silica gel eluting with 40% ethyl acetate in hexane to afford 5 contaminated with an olefinic by-product (total mass=6.5 g).

This sample of impure 5 was dissolved in a solution of acetone (59 mL) and water (7 mL). 4-Methylmorpholine N-oxide (3.81 g, 32 mmol) and osmium tetraoxide (4 mL of a 2.5 wt. % solution in t-butanol) were added, and the mixture was stirred for 19 h. Saturated sodium bisulfite (100 mL) and methylene chloride (200 mL) were added and a brown precipitate formed which was removed by filtration. The phases were separated, the aqueous was extracted with methylene chloride, the combined organic layers were dried (sodium sulfate), filtered, concentrated, and chromatographed on 300 g of silica gel eluting with 40% ethyl acetate in hexane to afford 5 (4.4 g, 41% yield from 4). $^{13}$C NMR (CDCl$_3$) δ 176.44 (C), 135.53 (CH), 135.50 (CH), 133.16 (C), 133.03 (C), 129.93 (CH), 129.86 (CH), 127.83 (CH), 127.79 (CH), 95.63 (d, J=174 Hz, CH), 83.91 (CH), 61.56 (d, J=7 Hz, CH$_2$), 52.66 (d, J=19 Hz, CH), 40.25 (CH), 40.24 (d, J=22 Hz, CH$_2$), 34.25 (CH$_2$), 26.82 (CH$_3$), 19.15 (C).

E. (3aR,4R,5S,6aS)-4-[(t-Butyldiphenylsiloxy)methyl]-5-fluoro-2-hydroxyhexahydro-2H-cyclopenta[b]furan (6)

To a solution of 5 (989 mg, 2.40 mmol) in toluene (15 mL) at −78° C. (bath temperature) was added dropwise a 1.5 M solution of diisobutylaluminum hydride in toluene (2.4 mL, 3.6 mmol). After 1 h, methanol (2 mL) and ethyl acetate (2 mL) were added, the solution was warmed to room temperature, added to saturated sodium potassium tartrate (30 mL), and stirred for 30 min. The layers were separated, the aqueous phase was extracted with ethyl acetate (3×30 mL), dried (magnesium sulfate), filtered, concentrated, and chromatographed on a 10 cm tall×26 mm diameter silica gel column eluting with 40% ethyl acetate in hexane to afford 6 (832 mg, 84%).

F. (5Z)-(9S, 11S)-13-(t-Butyldiphenylsiloxy)-11-fluoro-9-hydroxy-14,15,16,17,18,19,20-heptanor-5-prostenoic acid isopropyl ester (7)

To a suspension of (4-carboxybutyl) triphenylphosphonium bromide (2.05 g, 4.63 mmol) in tetrahydrofuran (17 mL) at 0° C. (bath temperature) was added a 1 M solution of potassium t-butoxide in tetrahydrofuran (9.6 mL, 9.6 mmol). After 15 min, a solution of 6 (832 mg, 2.01 mmol) in tetrahydrofuran (10 mL) was added. After 90 min, saturated ammonium chloride (25 mL) was added, the mixture was extracted with ethyl acetate (3×35 mL), dried (magnesium sulfate), filtered, and concentrated. The residue was dissolved in acetone (18 mL), cooled to 0° C. (bath temperature), and DBU (1.83 g, 12.1 mmol) was added. After 20 min, isopropyl iodide (2.05 g, 12.1 mmol) was added, and the mixture was warmed to room temperature and stirred overnight. Saturated ammonium chloride (25 mL) was added, the mixture was extracted with ether (3×25 mL), dried (magnesium sulfate), filtered, concentrated, and chromatographed on a 19 cm tall×26 mm diameter silica gel column to afford 7 (781 mg, 68%).

G. (5Z)-(9S, 11S)-13-(t-Butyldiphenylsiloxy)-11-fluoro-9-(tetrahydropyran-2-yloxy)-14,15,16,17,18,19,20-heptanor-5-prostenoic acid isopropyl ester (8)

To a mixture of 7 (780 mg, 1.44 mmol), methylene chloride (9 mL), and 3,4-dihydro-2H-pyran (184 mg, 2.20 mmol) at 0° C. (bath temperature) was added p-toluenesulfonic acid monohydrate (58 mg, 0.31 mmol). After 18 h, saturated sodium bicarbonate (20 mL) was added, the solution was extracted with methylene chloride (2×20 mL), dried (magnesium sulfate), filtered, concentrated, and chromatographed on a 15 cm tall×26 mm diameter silica gel column eluting with 20% ethyl acetate in hexane to afford 8 (687 mg, 76%).

H. (5Z)-(9S,11S)-11-Fluoro-13-hydroxy-9-(tetrahydropyran-2-yloxy)-14,15,16,17,18,19,20-heptanor-5-prostenoic acid isopropyl ester (9)

To a solution of 8 (683 mg, 1.09 mmol) in tetrahydrofuran (10 mL) was added a 1M solution of tetra-n-butylammonium fluoride (TBAF) (1.5 mL, 1.5 mmol). After 18 h, saturated ammonium chloride (25 mL) was added, the solution was extracted with ethyl acetate (3×25 mL), dried (magnesium sulfate), filtered, concentrated, and chromatographed on a 16 cm tall×26 mm diameter silica gel column eluting with 40% ethyl acetate in hexane to afford 9 (356 mg, 85%).

I. (5Z)-(9S, 11S)-11-Fluoro-13-oxo-9-(tetrahydropyran-2-yloxy)-14,15,16,17,18,19,20-heptanor-5-prostenoic acid isopropyl ester (10)

To a 2 M solution of oxalyl chloride in methylene chloride (0.54 mL, 1.08 mmol) in an additional 2 mL of methylene chloride at −78° C. (bath temperature) was added a solution of dimethyl sulfoxide (110 mg, 1.4 mmol) in methylene chloride (1 mL). After 15 min, a solution of 9 (287 mg, 0.74 mmol) in methylene chloride (4 mL) was added, and after an additional 20 min triethylamine (360 mg, 3.6 mmol) was added. The solution was warmed to room temperature, saturated ammonium chloride (20 mL) was added, the mixture was extracted with methylene chloride (2×20 mL), dried (magnesium sulfate), filtered, concentrated, and chromatographed on a 16 cm tall×26 mm diameter silica gel column eluting with 40% ethyl acetate in hexane to afford 10 (261 mg, 92%).

J. (5Z,13E)-(9S,11 S)-11-Fluoro-15-(2-indanyl)-15-oxo-9-(tetrahydropyran-2-yloxy)-16,17,18,19,20-pentanor-5,13-prostadienoic acid isopropyl ester (11)

To a solution of lithium chloride (107 mg, 2.54 mmol), triethylamine (116 mg, 1.15 mmol), and dimethyl 2-oxo-2-(2-indanyl)ethylphosphonate (420 mg, 1.57 mmol) in THF (4 mL) at 0° C. (bath temperature) was added a solution of aldehyde 10 (300 mg, 0.78 mmol). The reaction was warmed to room temperature and stirred overnight. Saturated ammonium chloride (10 mL) was added, the mixture was extracted with ethyl acetate (3×10 mL), dried (magnesium sulfate), filtered, concentrated, and chromatographed on a 16 cm tall×26 mm diameter silica gel column eluting with 20% ethyl acetate in hexane to afford 11 (351 mg, 85%).

K. (5Z,13E)-(9S,11 S,15R)-11-Fluoro-15-hydroxy-15-(2-indanyl)-9-(tetrahydropyran-2-yloxy)-16,17,18,19,20-pentanor-5,13-prostadienoic acid isopropyl ester (12)

To a mixture of 11 (340 mg, 0.64 mmol), methanol (10 mL), and cerium trichloride heptahydrate (620 mg, 1.66 mmol) at 0° C. (bath temperature) was added sodium borohydride (40 mg, 1.05 mmol) in 3 portions. After 2.5 h, saturated potassium dihydrogen phosphate (10 mL) and water (10 mL) were added, the mixture was extracted with ethyl acetate (3×20 mL), dried (magnesium sulfate), filtered, and concentrated to afford 12 and the corresponding 15S diastereomer (340 mg combined, 100%).

L. (5Z, 13E)-(9S, 11S,15R)-9,15-Dihydroxy-11-fluoro-15-(2-indanyl)-16,17,18,19,20-pentanor-5,13-prostadienoic acid isopropyl ester (II)

To a solution of a mixture of 12 and the corresponding 15S diastereomer (340 mg combined, 0.64 mmol) in isopropanol (12 mL) was added a solution of 12 M HCl (1.1 mL). After 1 h 2 M sodium hydroxide (10 mL) was added, the layers were separated, the aqueous phase was extracted with ethyl acetate (2×15 mL), the combined organic layers were dried (magnesium sulfate), filtered, concentrated, and chromatographed on a 27 cm tall×26 mm diameter silica gel column eluting with 40% ethyl acetate in hexane to afford II (76 mg, 27%), as well as the corresponding 15S diastereomer (53 mg, 19%). $^{13}$C NMR (CDCl$_3$) δ 173.49 (C), 143.02 (C), 142.89 (C), 135.37 (CH), 129.94 (CH), 129.04 (CH), 128.80 (CH), 128.64 (CH), 126.15 (CH), 124.48 (CH), 124.35 (CH), 96.89 (d, J=174 Hz, CH), 76.12 (CH), 71.43 (CH), 67.75 (CH), 50.68 (d, J=18 Hz, CH), 47.51 (CH), 45.11 (CH), 42.85 (d, J=22 Hz, CH$_2$), 35.53 (CH$_2$), 35.34 (CH$_2$), 33.90 (CH$_2$), 26.62 (CH$_2$), 24.77 (CH$_2$), 24.59 (CH$_2$), 21.84 (CH$_3$). MS, m/z calcd. for C$_{27}$H$_{37}$O$_4$FNa [(M+Na)$^+$], 467; found, 467.

EXAMPLE 2

Synthesis of III

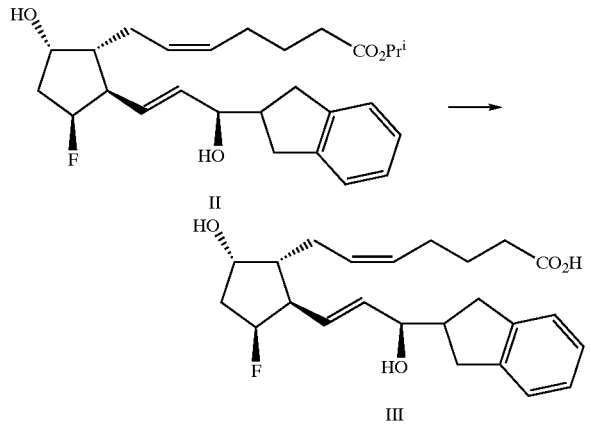

(5Z,13E)-(9S,11S,15R)-9,15-Dihydroxy-11-fluoro-15-(2-indanyl)-16,17,18,19,20-pentanor-5,13-prostadienoic acid (III)

To a mixture of II (28.2 mg, 0.063 mmol), methanol (3.5 mL), and water (0.5 mL) was added lithium hydroxide monohydrate (10 mg, 0.24 mmol). After 16 h a 1 M HCl solution was added (2 mL), the mixture was extracted with ethyl acetate (4×4 mL), concentrated, and chromatographed on a 15 cm tall×10 mm diameter silica gel column eluting with ethyl acetate to afford III (19.2 mg, 76%). $^{13}$C NMR (CDCl$_3$) δ 177.14 (C), 142.84 (C), 142.71 (C), 134.57 (CH), 129.96 (CH), 129.79 (CH), 129.62 (CH), 128.85 (CH), 126.23 (CH), 124.50 (CH), 124.37 (CH), 96.67 (d, J=174 Hz, CH), 76.79 (CH), 71.42 (CH), 50.95 (d, J=18 Hz, CH), 47.86 (CH), 45.06 (CH), 42.96 (d, J=22 Hz, CH$_2$), 35.61 (CH$_2$), 35.32 (CH$_2$), 32.49 (CH$_2$), 26.18 (CH$_2$), 24.36 (CH$_2$), 24.16 (CH$_2$).

FP prostaglandin receptors are found in many organs of the body and have been implicated in many disorders/diseases. In addition, it is now believed that some of the side-effects of FP prostaglandins when topically applied to treat glaucoma, such as ocular surface hyperemia, iris hyperpigmentation and cystoid macular edema in the retina, may result from activation of the FP receptor. The FP receptor antagonists of the present invention are therefore useful as therapeutic agents to combat the afore-mentioned side-effects. Other therapeutic uses of the FP antagonists of this invention would include treatment of any medical disorder or condition characterized by excessive FP receptor activation, regardless of whether such excessive activation is attributable to elevated FP agonist levels, increased numbers of receptors, or increased sensitivity of the receptors. Such uses include, without limitation, treatment of: acute and/or chronic inflammatory conditions, excessive bone deposition, benign prostatic hypertrophy, uterine cramps, irritable bowel disease, cardiac arrythmias, epilepsy or conditions resulting from the same, as well as prevention or ameliorating of certain degenerative diseases, and improving function of the immune system. Moreover, the FP receptor antagonists of the present invention may be used as diagnostic and/or pharmacological tools to demonstrate the mechanism of action of prostaglandins working through the FP receptor in vitro and/or in vivo. An example of how such an agent would be used in vitro is described below and also demonstrated in FIGS. 2–4.

The FP antagonists of the present invention may be conventionally formulated in the appropriate vehicle (e.g. water, gel, compressed tablet, etc. in the presence or absence of exipients as needed) suitable for topical ocular, oral, subcutaneous, intravenous or other routes of administration at the appropriate dose (e.g. 0.00003 to 1.0% for topical ocular use) determined by the physician/investigator skilled in the art. Depending on the purpose for which the compounds of this invention are used (e.g. for in vivo or in vitro antagonism of the FP receptor) and the method of their delivery, they may be used in one or more preferred chemical forms, for example, the ester and/or acylated alcohol pro-drugs of the core structures.

EXAMPLE 3

Measuring in Vitro Pharmacological Activity of FP Receptor Agonists and Antagonists Confluent monolayer cultures of cells (in a standard 24-well tissue culture plate) expressing the FP receptor are exposed to [$^3$H]-myo-inositol (1.5 μCi in a volume of 0.5 ml DMEM culture medium supplemented with 2 mM L-glutamine and 10 μg/ml gentamicin sulfate) in the absence of serum, which causes net incorporation of the radioisotope into the phosphotidylinositol membrane lipids. After 24–32 hrs, the medium with the radioisotope is removed and the cells are rinsed once with DMEM/F-12 medium containing 10 mM LiCl (assay medium). Then 0.5 ml of assay medium is added to each well of cells, followed by addition of varying concentrations of an FP receptor agonist (or other test compound). Cells are exposed to the test agent for 30–120 mm in a humidified incubator (95% air/5% CO$_2$), maintained at 37° C. Then the assay medium is removed and 1 ml of 0.1 M formic acid is added to the cell monolayer to inactivate the phospholipase C and to release the radiolabelled products into the assay medium. The presence of LiCl during the agonist stimulation period inhibits phosphatases and permits the accumulation of radiolabelled inositol phosphates (IPs) which is measured by ion exchange chromatography.

The agonist-dependent production of IPs, which reflects the degree of receptor activation, is quantitatively measured for each well of cells in the 24-well plate by separating the negatively charged radiolabelled IPs from other minor radiolabelled species and free [$^3$H]-myo-inositol by anion exchange chromatography. This is accomplished by adding 0.9 ml of the cell lysate obtained as described above to a column packed with 1 ml of AG 1-X8 anion exchange resin in the formate form. The elution and separation of the radiolabelled IPs from the column consists of sequential additions to the column of: 1) 10 ml of water; 2) 8 ml of 50 mM ammonium formate; and 3) 4 ml of 1.2 M ammonium formate solution containing 0.1 M formic acid. The first two washes are discarded, and the third is collected in a scintillation vial, to which is added 15 ml of a water-accepting scintillation fluid. These samples, i.e., the radiolabelled IPs formed by the cells in response to stimulation by an FP prostaglandin receptor agonist or other test agent, is then measured by scintillation spectrometry on a beta-counter.

The dependence of the level of the [$^3$H]IPs production on agonist concentration is analyzed by standard pharmacological methods to determine the potency (EC$_{50}$ value) and efficacy (maximum response; E$_{max}$) of the FP receptor agonist relative to a standard FP receptor agonist such as fluprostenol. The partial agonist activity of Compound III at the FP receptor is shown in FIG. 1. Compound III is classified as a partial agonist because the maximum effect of this compound is substantially lower than that of the reference (full agonist) compounds, cloprostenol or fluprostenol (FIG. 1). For the evaluation of putative antagonists of the formation of IPs, cells are pre-incubated for 10–20 min with the putative antagonist (in this case Compound III) prior to adding the agonist, typically one of the more potent and selective FP agonists like cloprostenol or fluprostenol. The agonist stimulation is then continued for the standard time (30–120 min), after which the procedure for quenching the reaction, separating the [$^3$H]IPs, and anion exchange chromatography is identical to the procedure described above. A compound is considered to be an antagonist in this protocol if it inhibits the agonist-stimulated [$^3$H]IPs production relative to the production measured in the control experiment (performed in parallel), in which the solvent is substituted for the antagonist.

Figure 4:
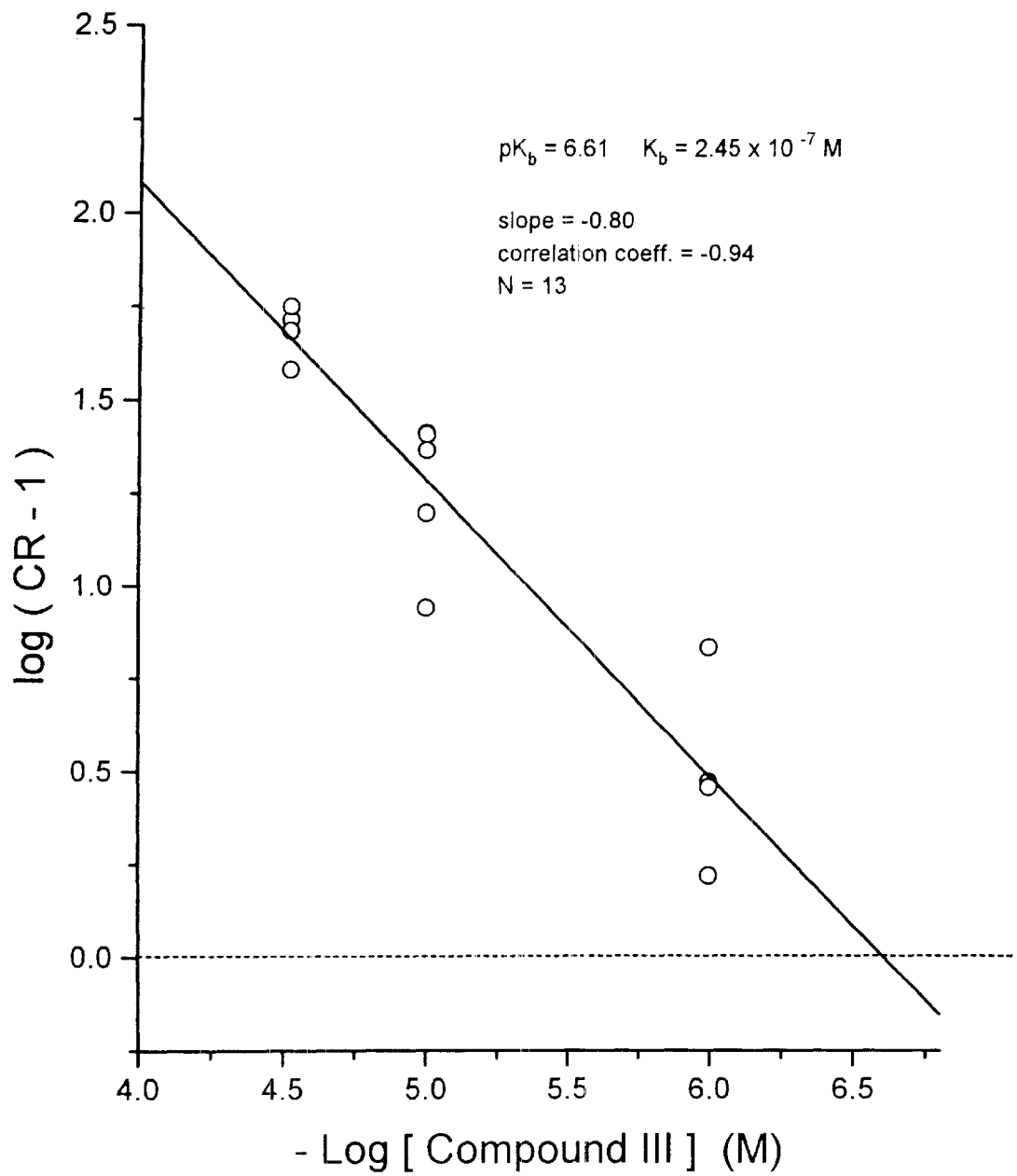
FIG. 4 is a graphical depiction of a Schild analysis for Compound III as an FP receptor antagonist.
Figure 5:
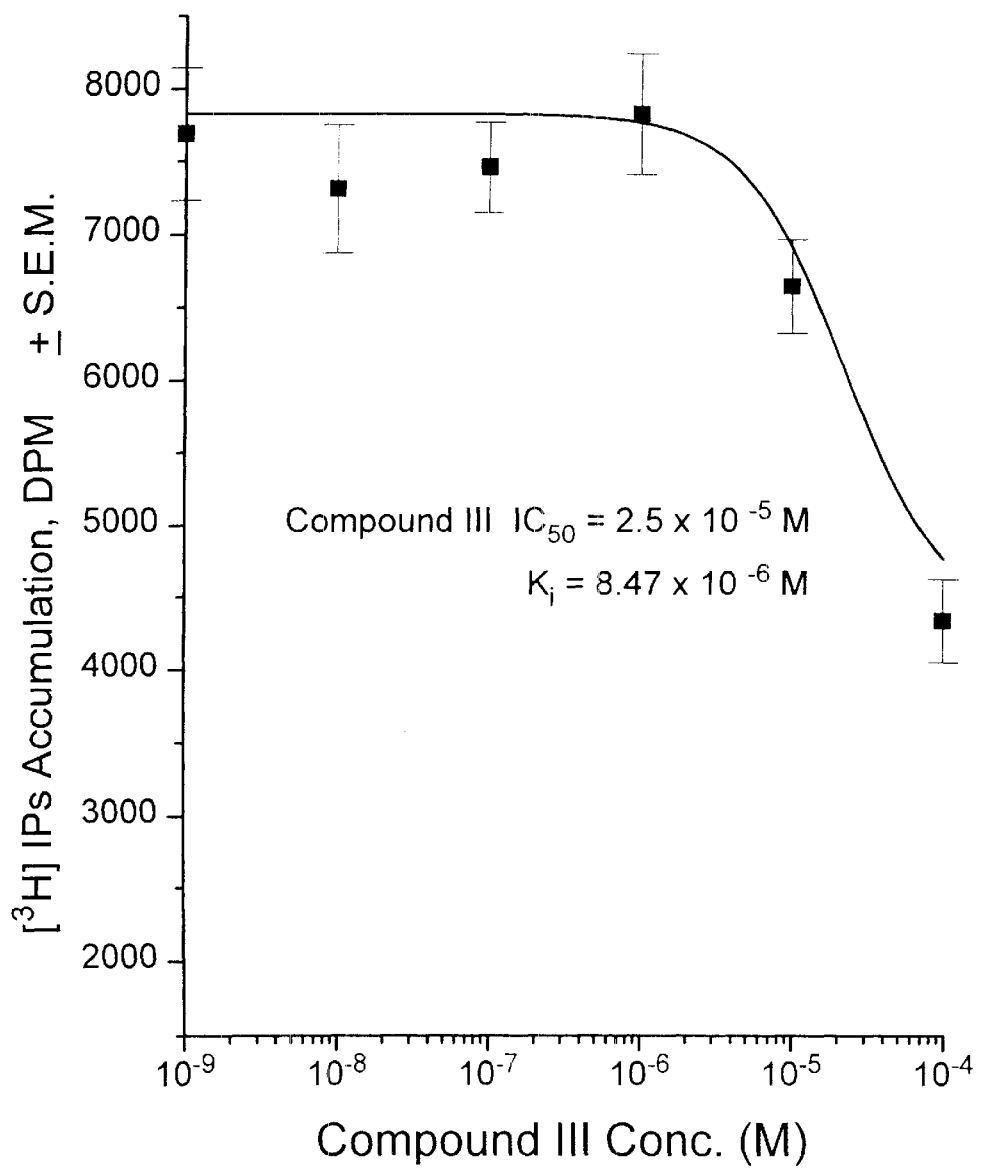
FIG. 5 is a graphical depiction of the concentration dependent inhibition by Compound III of human ocular FP receptor functional response.

Two different antagonist protocols are employed: 1) the antagonist concentration is varied while holding the agonist concentration fixed at a concentration approximately 10 times the agonist EC$_{50}$ value and 2) the antagonist concentration is fixed in a given experiment, with the agonist concentration varied, and several such experiments, each with a different, fixed antagonist concentration, are performed. The first protocol yields an inhibition constant (IC$_{50}$ value) for the antagonist (as illustrated for Compound III in FIG. 2). Since Compound III was a partial agonist, it exhibited antagonist properties under this experimental regimen. The second protocol establishes the effect of increasing antagonist concentration on the agonist EC$_{50}$ value (as illustrated for Compound III in FIG. 3. At increasing concentrations, Compound III progressively shifted the dose-response curves of fluprostenol-induced [$^3$H]IPs production in A7r5 cells. Since the maximal effects of fluprostenol were unaltered, while its potency was reduced in the presence of the increasing concentrations of Compound III, the latter compound can be classified as a "competitive antagonist". Schild analysis of data from the second protocol yields quantitative antagonist potency data (as illustrated for Compound III in FIG. 4 and Table 1). FIG. 4 includes data from several experiments of the type described in FIG. 3. The transformed data in FIG. 4 indicate that the antagonist properties of Compound III were highly reproducible (n=4 experiments) and the potency of the compound determined by this method (K$_b$=285±97 nM) compared well with that determined by the method shown in FIG. 2 (K$_i$=426±63 nM). Overall, the K$_i$ and Kb values are synonymous and represent the antagonist potency of the antagonist at equilibrium. Two cell lines containing the FP receptor have been extensively characterized by this method, using known potent FP receptor agonists, as well as prostaglandins known to have some selectivity for other classes of prostaglandin receptors. These cell lines, available from the American Type Culture Collection, are the Swiss 3T3 embryonic albino mouse fibroblast line and the A7r5 rat thoracic aorta smooth muscle cell line. Another cell-line expressing the recombinant human ocular FP receptor (HEK-293; human embryonic kidney), generated by techniques well known to those skilled in the art, was also used to confirm the FP-antagonism of Compound III. As shown in FIG. 5, this compound behaved as an antagonist of fluprostenol-induced [$^3$H]IPs production, thereby confirming its potency against the human ocular FP receptor.

TABLE 1

Potencies of Compounds Evaluated as Antagonists of the FP Receptor (A7r5 Cells)

| Compound | K$_b$, mol/L |
|---|---|
| Compound III | 2.5 × 10$^{-7}$ |
| PGF$_{2\alpha}$ dimethyl amide | Inactive |
| PGF$_{2\alpha}$ dimethyl amine | Inactive |
| Tolbutamide | Inactive |
| Glibenclamide | 1.6 × 10$^{-4}$ |
| Phloretin | 5.2 × 10$^{-6}$ |

The data in Table 1 indicate that Compound III has greater than the 10-fold higher potency as an FP receptor antagonist than phloretin, and that the other FP receptor antagonists are considerably less potent or inactive (e.g., tolbutamide, PGF$_{2\alpha}$ dimethyl amide and PGF$_{2\alpha}$ dimethyl amine). Also, Compound III, unlike phloretin, has relatively good selectivity for the FP prostaglandin receptor, compared to other classes of prostaglandin receptors.

EXAMPLE 4

Figure 2:
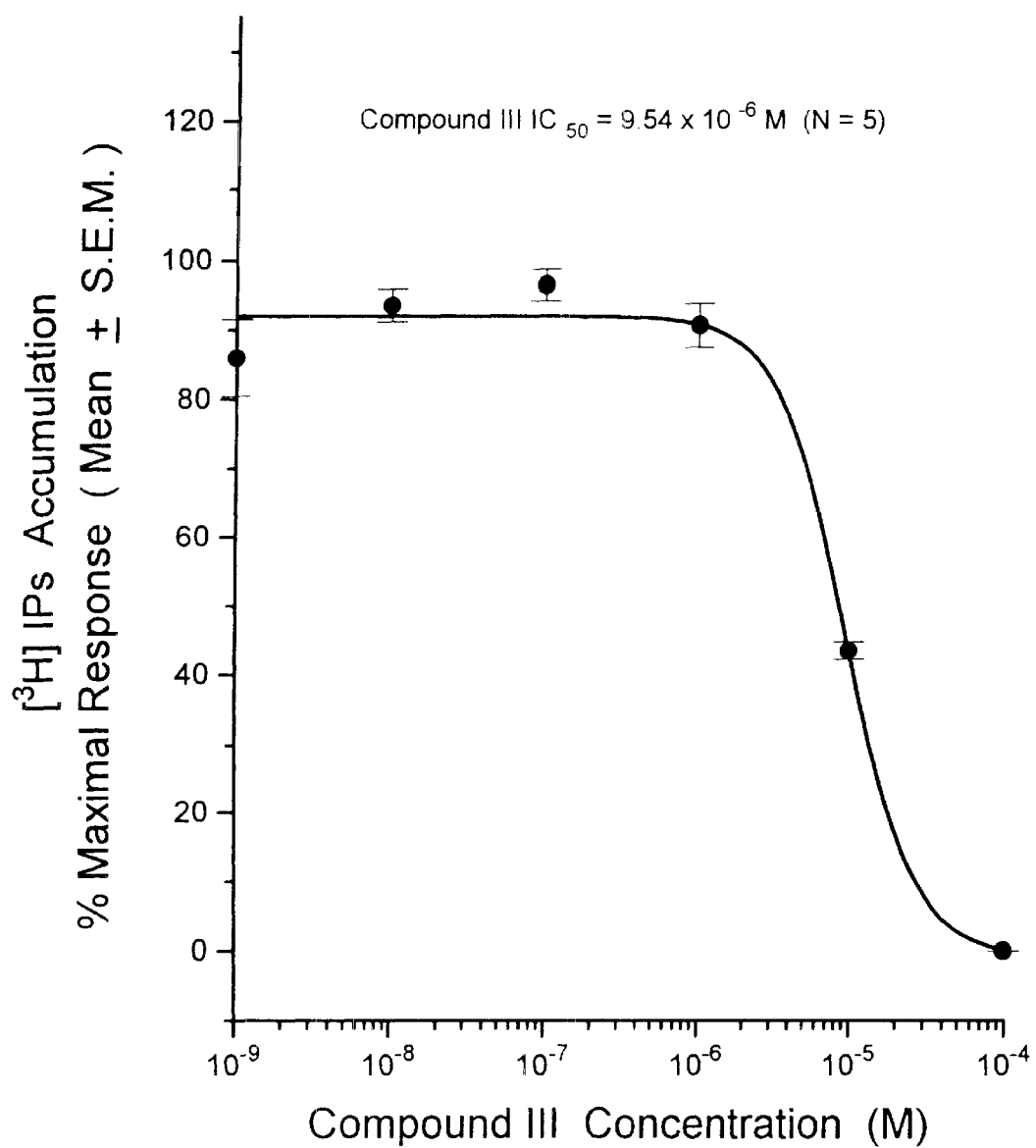
FIG. 2 is a graphical depiction of the concentration-dependent inhibition by Compound III of the fluprostenol-stimulated [$^3$H]IPs production in A7r5 cells.
Figure 3:
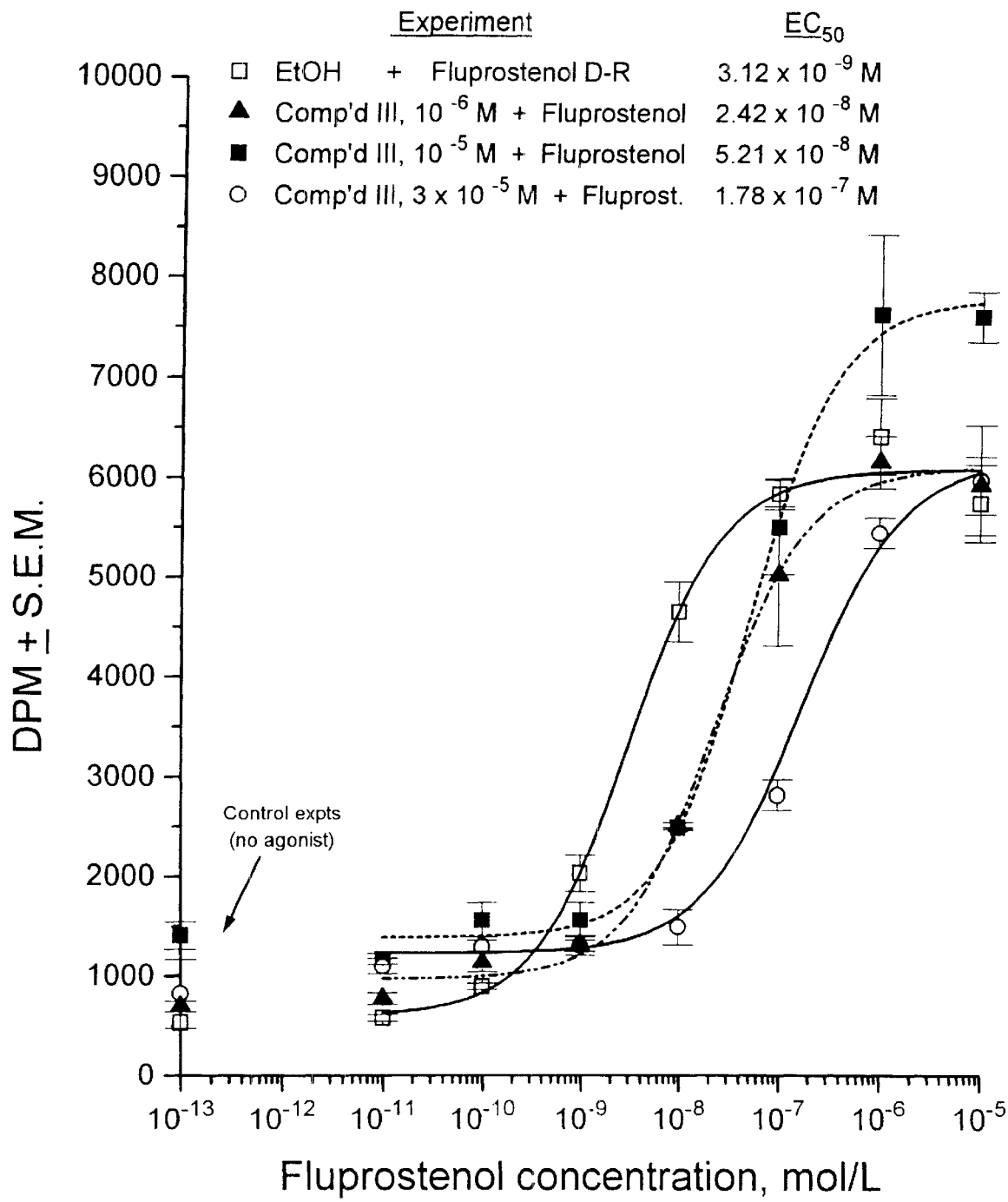
FIG. 3 is a graphical depiction of the antagonist properties of Compound III.

In order to determine if a test compound is an FP agonist, the type of experiment illustrated by FIGS. 2 and 3 is performed. Compound III (at 10 nM to 100 μM final concentrations) is added to [$^3$H]myo-inositol-labeled cells expressing an FP receptor 10–20 min prior to adding the test compound (at a fixed concentration which produces >50% of the maximal response) in the presence of 10 mM LiCl. The reaction is stopped and the [$^3$H]IPs produced in each well of the culture plate are determined by ion exchange chromatography as previously described in Example 3. The unknown agent's actions are found to be concentration-dependently inhibited by Compound III and the Schild-type experimental regimen (as exemplified in FIGS. 3 and 4) also yields the appropriate inhibition profile by Compound III. The unknown agent is therefore reliably classified as an FP agonist acting through an FP receptor-mediated signal transduction cascade.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of antagonizing FP receptors, comprising exposing such receptors to a compound of formula I:

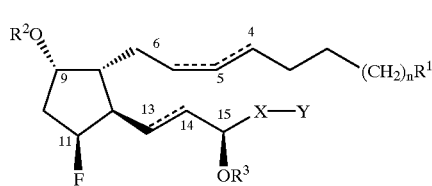

wherein:
R$^1$=CO$_2$R, CONR$^4$R$^5$, CH$_2$OR$^6$, or CH$_2$NR$^7$R$^8$; where:
R=H or cationic salt moiety, or CO$_2$R=pharmaceutically acceptable ester moiety; R$^4$, R$^5$=same or different=H or alkyl; R$^6$=H, acyl or alkyl; R$^7$, R$^8$=same or different=H, acyl, or alkyl; with the proviso that if one of R$^7$, R$^8$=acyl, then the other=H or alkyl;
n=0 or 2;
R$^2$, R$^3$=same or different=H, alkyl, or acyl;
----=single or non-cumulated double bond, with the provisos that if a double bond is present between carbons 4 and 5, it is of the cis configuration; and that if a double bond is present between carbons 13 and 14, it is of the trans configuration;
X=(CH$_2$)$_m$ or (CH$_2$)$_m$O, where m=1–6; and
Y=phenyl, optionally substituted with alkyl, halo, trihalomethyl, alkoxy, acyl, acyloxy, amino, alkylamino, acylamino, or hydroxy; or
X-Y=(CH$_2$)$_p$Y$^1$; where p=0–6; and

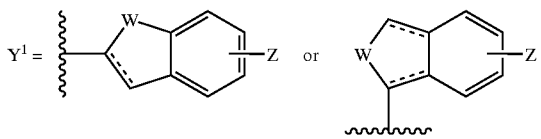

wherein:
W=CH$_2$, O, S(O)$_q$, NR$^{10}$, CH$_2$CH$_2$, CH=CH, CH$_2$O, CH$_2$S(O)$_q$, CH=N, or CH$_2$NR$^9$; where q=0–2, and R$_{10}$ H, alkyl, or acyl;
Z=H, alkyl, alkoxy, acyl, acyloxy, halo, trihalomethyl, amino, alkylamino, acylamino, or hydroxy; and
----=single or double bond.

2. The method of claim 1, wherein for the compound of formula I:
R$^1$=CO$_2$R, CONR$^4$R$^5$, CH$_2$OR$^6$, or CH$_2$NR$^7$R$^8$; where:
R=H or cationic salt moiety, or CO$_2$R=pharmaceutically acceptable ester moiety; R$^4$, R$^5$=same or different=H or alkyl; R$^6$=H, acyl, or alkyl; R$^7$, R$^8$=same or different=H, acyl, or alkyl; with the proviso that if one of R$^7$, R$^8$=acyl, then the other=H or alkyl;
n=0 or 2;
R$^2$, R$^3$=same or different=H, alkyl, or acyl;
----=single or non-cumulated double bond, with the provisos that if a double bond is present between carbons 4 and 5, it is of the cis configuration; and that if a double bond is present between carbons 13 and 14, it is of the trans configuration; and
X-Y=(CH$_2$)$_p$Y$_1$; where p=0–6; and

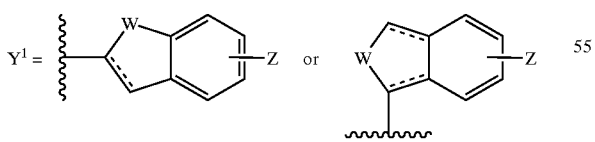

wherein:
W=CH$_2$, O, S(O)$_q$, NR$^{10}$, CH$_2$CH$_2$, CH=CH, CH$_2$O, CH$_2$S(O)$_q$, CH=N, or CH$_2$NR ; where q=0–2, and R$^{10}$=H, alkyl, or acyl;
Z=H, alkyl, alkoxy, acyl, acyloxy, halo, trihalomethyl, amino, alkylamino, acylamino, or hydroxy; and
----=single or double bond.

3. The method of claim 2, wherein for the compound of formula I:
R$^1$=CO$_2$R, where R=H; or CO$_2$R=pharmaceutically acceptable ester moiety;
n=0;
R$^2$=R$^3$=H;
----=single or non-cumulated double bond, with the provisos that if double bond is present between carbons 4 and 5 or carbons 5 and 6, it is of the cis configuration; and that if a double bond is present between carbons 13 and 14, it is of the trans configuration; and
X-Y=(CH$_2$)$_p$Y$^1$; where p=0; and

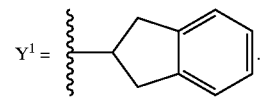

4. The method of claim 3, wherein the compound is:

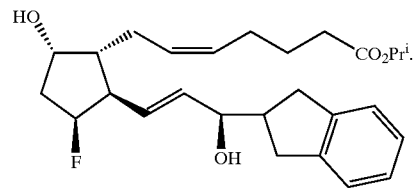

5. The method of claim 3, wherein the compound is:

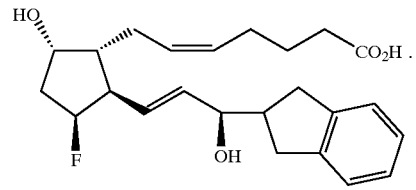

6. A method of determining whether a test compound is an FP agonist, comprising:
(i) providing a culture of FP receptor containing cells that produce FP receptor product when activated; and (ii) comparing the amount of FP receptor product produced when the culture of cells is exposed to the test compound in the absence of an FP antagonist with the amount of FP receptor product produced when the culture of cells is exposed to the test compound in the presence of an FP receptor antagonizing effective amount of a compound of formula I:

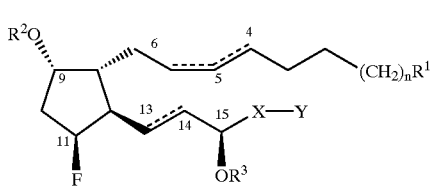

wherein:
R$^1$=CO$^2$R, CONR$^4$R$^5$, CH$_2$OR$^6$, or CH$_2$NR$^7$R$^8$; where:
R=H or cationic salt moiety, or CO$^2$R=pharmaceutically acceptable ester moiety; R$^4$, R$^5$=same or different=H or alkyl; R$^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

$R^2$, $R^3$=same or different=H, alkyl, or acyl;

----=single or non-cumulated double bond, with the provisos that if a double bond is present between carbons 4 and 5, it is of the cis configuration; and that if a double bond is present between carbons 13 and 14, it is of the trans configuration;

X=$(CH_2)_m$ or $(CH_2)_mO$, where m=1–6; and

Y=phenyl, optionally substituted with alkyl, halo, trihalomethyl, alkoxy, acyl, acyloxy, amino, alkylamino, acylamino, or hydroxy; or X-Y=$(CH_2)_pY^1$; where p=0–6; and

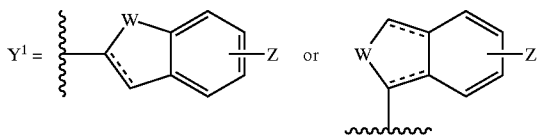

wherein:

W=$CH_2$, O, $S(O)_q$, $NR^{10}$, $CH_2CH_2$, CH=CH, $CH_2O$, $CH_2S(O)_q$, CH=N, or $CH_2NR^9$; where q=0–2, and $R^{10}$=H, alkyl, or acyl;

Z=H, alkyl, alkoxy, acyl, acyloxy, halo, trihalomethyl, amino, alkylamino, acylamino, or hydroxy; and ----=single or double bond.

7. The method of claim 6 wherein for the compound of formula I:

$R^1$=$CO^2R$, $CONR^4R^5$, $CH_2OR^6$, or $CH_2NR^7R^8$; where:
R=H or cationic salt moiety, or $CO_2R$= pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

$R^2$, $R^3$=same or different=H, alkyl, or acyl;

----=single or non-cumulated double bond, with the provisos that if a double bond is present between carbons 4 and 5, it is of the cis configuration; and that if a double bond is present between carbons 13 and 14, it is of the trans configuration; and X-Y $(CH_2)_pY^1$; where p=0–6; and

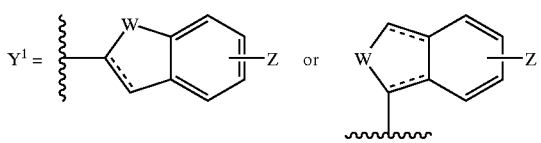

wherein:

W=$CH_2$, O, $S(O)_q$, $NR^{10}$, $CH_2CH_2$, CH=CH, $CH_2O$, $CH_2S(O)_q$, CH=N, or $CH_2NR^9$; where q=0–2, and $R^{10}$=H, alkyl, or acyl;

Z=H, alkyl, alkoxy, acyl, acyloxy, halo, trihalomethyl, amino, alkylamino, acylamino, or hydroxy; and ----=single or double bond.

8. The method of claim 7, wherein for the compound of formula I:

$R^1$=$CO_2R$, where R=H; or $CO_2R$=pharmaceutically acceptable ester moiety;

n=0;

$R^2$=$R^3$=H;

----=single or non-cumulated double bond, with the provisos that if double bond is present between carbons 4 and 5 or carbons 5 and 6, it is of the cis configuration; and that if a double bond is present between carbons 13 and 14, it is of the trans configuration; and X-Y=$(CH_2)_pY^1$; where p=0; and

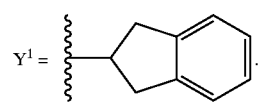

9. The method of claim 8, wherein the compound is:

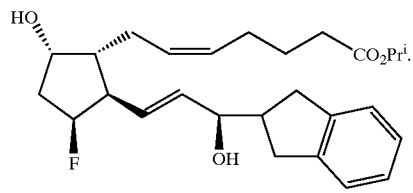

10. The method of claim 8, wherein the compound is:

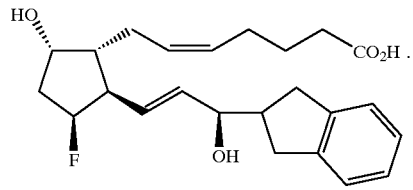

11. The method of claim 6, wherein the FP receptor product is an inositol phosphate.

12. The method of claim 11, wherein the inositol phosphate is inositol 1,4,5-trisphosphate.

13. The method of claim 6, wherein the FP receptor product is diacyl glycerol.

14. The method of claim 6, wherein the FP receptor product is intracellular calcium.

15. The method of claim 6, wherein the FP receptor product is an activator of a protein kinase.

16. The method of claim 15, wherein the protein kinase is protein kinase C.

* * * * *